US00PP13756P29

(12) United States Plant Patent
Danziger

(10) Patent No.: US PP13,756 P2
(45) Date of Patent: Apr. 29, 2003

(54) GYPSOPHILA PLANT NAMED 'DANGYPFUN'

(75) Inventor: Gabriel Danziger, Nir-Zvi (IL)

(73) Assignee: Danziger - "DAN" Flower Farm, Moshav Mishmar Hashiva (IL)

( * ) Notice: Subject to any disclaimer, the term of this patent is extended or adjusted under 35 U.S.C. 154(b) by 28 days.

(21) Appl. No.: 09/984,618

(22) Filed: Oct. 30, 2001

(51) Int. Cl.[7] ..... A01H 5/00

(52) U.S. Cl. ..... Plt./354
(58) Field of Search ..... Plt./354

*Primary Examiner*—Kent Bell
(74) *Attorney, Agent, or Firm*—Foley & Lardner

(57) ABSTRACT

A new and distinct Gypsophila plant named 'Dangypfun' characterized by having semi double, white flowers, very small, 4–5 mm diameter, 1500–2000 flowers per stem; buds remain unfolded for several days; flowers arranged in clusters, maintain stablility during hot season, 80–90 cm in height, open formation; apical dominance growth; 10–14 days cut flower longevity.

2 Drawing Sheets

LATIN NAME OF THE GENUS AND SPECIES OF THE PLANT CLAIMED

*Gypsophila paniculata.*

VARIETY DENOMINATION

'Dangypfun'.

BACKGROUND OF THE INVENTION

The present invention relates to a new and distinct cultivar of Gypsophila plant, botanically known as *Gypsophila paniculata*, hereinafter referred to by the cultivar name 'Dangypfun'.

'Dangypfun' is a spontaneous branch mutation of cultivar Gypsophila 'Dangypmini' (U.S. Plant Pat. No. 10,964) selected in a cultivated environment in Moshav Mishmar Hashiva, Israel by the inventor, Gabriel Danziger. Asexual reproduction of the new cultivar by side shoot cutting was first performed in January, 2001, in Moshav Mishmar Hashiva, Israel and has demonstrated that the combination of characteristics as herein disclosed for the new cultivar are firmly fixed, reproduce true to type, and are retained through successive generations of asexual reproduction.

BRIEF DESCRIPTION OF THE INVENTION

The following traits have been repeatedly observed and are determined to be basic characteristics of 'Dangypfun' which in combination distinguish this Gypsophila as a new and distinct cultivar:

1. Semi double, white flowers, very small, 4–5 mm diameter, 1500–2000 flowers per stem;
2. Buds remain unfolded for several days;
3. Flowers arranged in clusters, maintain stability during hot season, plant height of 80–90 cm, open formation;
4. Apical dominance growth habit;
5. 10–14 days cut flower longevity.

'Dangypfun' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Moshav Mishmar Hashiva, Israel under conditions which closely approximate those generally used in commercial practice.

Of the many commercial cultivars known to the present inventor, the most similar in comparison to 'Dangypfun' is the cultivar 'Dangypmini'. In comparison to 'Dangypmini', flowers of 'Dangypfun' are smaller by 1–2 mm and have less petals during low light intensities. The fully developed buds of 'Dangypfun' remain unfolded for several days whereas fully developed buds of 'Dangypmini' open immediately. The flowering time of 'Dangypfun' is on average one week later than 'Dangypmini'.

BRIEF DESCRIPTION OF THE DRAWING

The accompanying photographic drawings show typical flower and foliage characteristics of 'Dangypfun' with colors being as true as possible will illustrations of this type.

The first drawing is a close-up view of a flowering stem segment, and the second drawing shows a flowering stem of the instant plant.

DETAILED BOTANICAL DESCRIPTION

The following observations, measurements and values describe the new cultivar 3 months from planting as grown in Moshav Mishmar hashiva, Israel under conditions which closely approximate those generally used in commercial practice recommended for Gypsophila plants, in open field during summer and in a protected greenhouse during winter. The minimum temperature during winter is 15° C., the summer temperature ranging from 18–40° C. Color references are made to The Royal Horticultural Society Colour Chart (R.H.S.), except where general colors of ordinary significance are used.

Propagation: Side shoot cuttings.
Plant:

*General appearance and form.*—Height: 80–90 cm. Width: 70–80 cm. Habit: Apical dominance. Form: Bush upright. Flowering Response: During long day conditions. Flowering Season: Spring, summer and fall, in winter only with supplemental lighting.

Vigor/Growth rate: In summer flowers 9–10 weeks after planting, in winter flowers 13–14 weeks after planting.

*Winter hardiness.*—When grown in an open field, temperatures down to 0° C. are withstood.

*Lastingness of the individual bloom.*—10–14 days on the plant, depending on weather conditions; 10–14 days for cut flowers at room temperature, after harvesting flowering stems and treating them commercially.

*Rooting.*—Application of rooting hormone, kept wet, direct sunlight avoided.

*Fragrance.*—Typical of Gypsophila.

Foliage:

*Overall shape of leaf.*—Lanceolate. Base: Truncate. Tip: Acuminate.

*Margin.*—Entire.

*Texture.*—Rough.

*Main color of upper surface.*—Mature leaf: Green 139 A. Immature leaf: Green 139 A.

*Main color of lower surface.*—Mature leaf: Green 137 A. Immature leaf: Green 137 A.

*Venation color.*—None.

*Size.*—Length: 6–7 cm. Width: 10–12 mm.

*Stipules.*—None.

*Attachment.*—Sessile.

Inflorescence:

*Natural flowering season.*—Spring, summer and fall, during long day conditions.

*Corolla.*—Form: Ball shaped. Shape: Ball shaped. Average Number of Flowers: 1500–2000. Size: 4–5 mm diameter.

*Petals.*—Number: 44–45 after long day period with high light intensity. 25–30 after short day period with low light intensity. Shape: Lanceolate with emarginate tip. Size: 2 mm length, 1 mm width. Markings: None. Color: Upper surface: White 155 D. Lower surface: White 155 D.

*Sepals.*—Number: 5. Shape: Lanceolate. Length: 2 mm. Apex: Acuminate. Margin: Entire. Color: Green RHS 143 A (both upper and lower surfaces).

Stem:

*Quanity.*—6–8 stems per plant.

*Average length.*—80–90 cm.

*Average diameter.*—4–5 mm.

*Color.*—Green 143 B.

*Internode length.*—4–7 cm.

Bud:

*Response.*—Long day conditions.

*Color.*—White 155 D.

*Size before opening.*—2 mm diameter, 3 mm length.

*Shape.*—Obovate to round.

Pedicel:

*Length.*—4–6 mm.

*Diameter.*—0.5 mm.

*Color.*—Green 143 B.

Reproductive organs: Not visible.

Disease resistance: Not susceptible to most pests and diseases under regular growing conditions.

I claim:

1. A new and distinct Gypsophila plant named 'Dangypfun', substantially as illustrated and described herein.

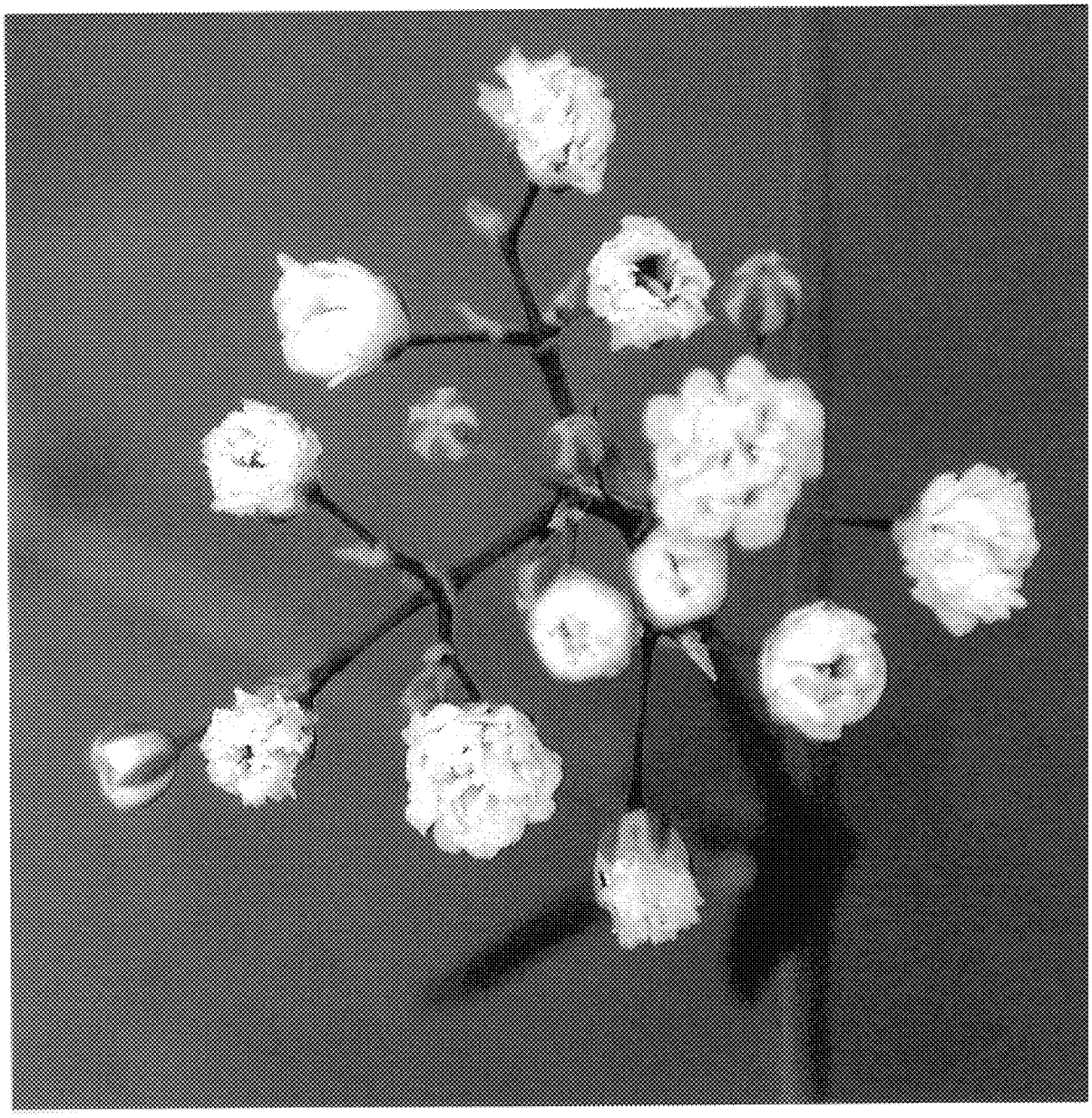

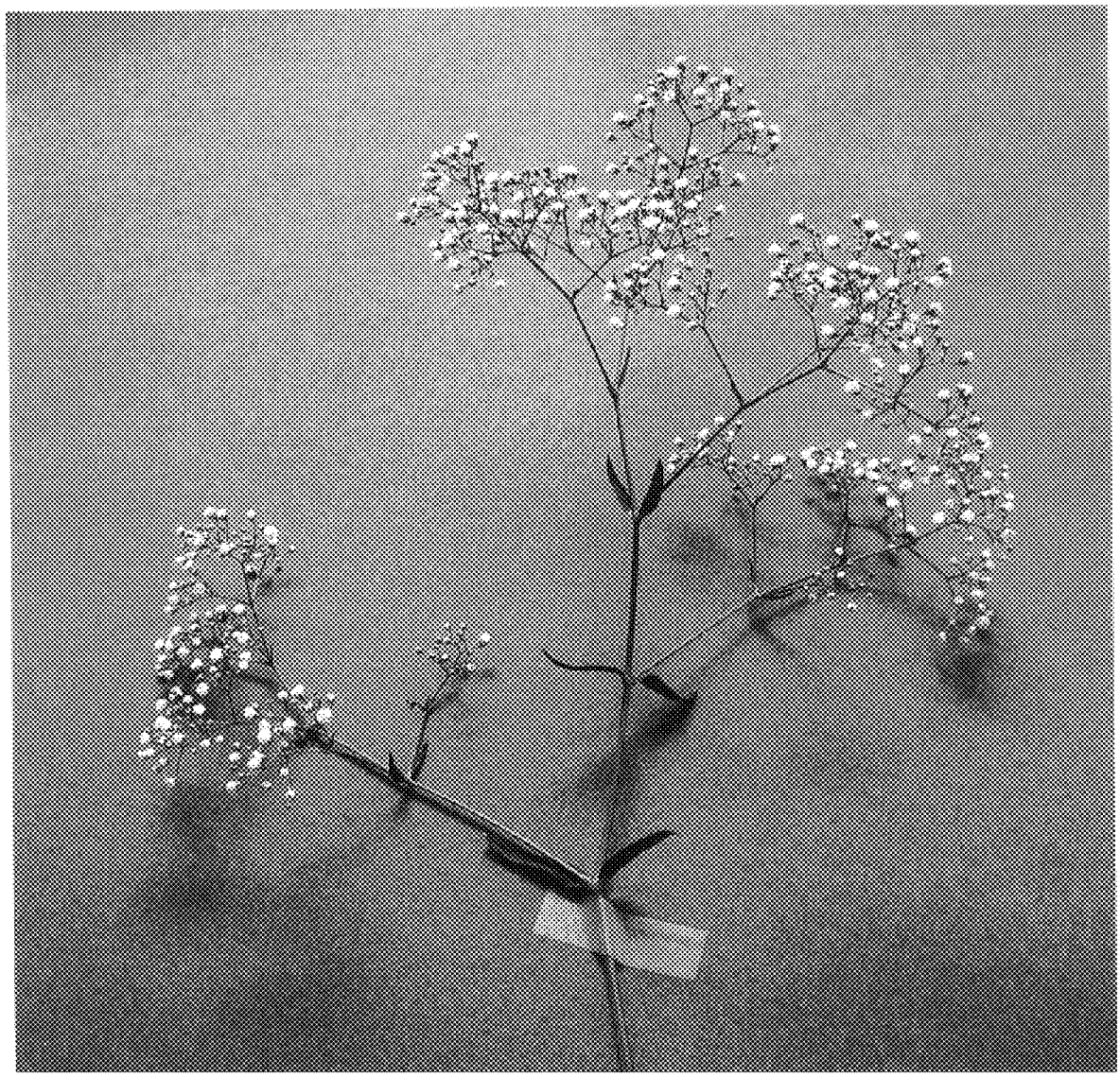

* * * * *